United States Patent [19]

Lavin et al.

[11] Patent Number: 5,347,822
[45] Date of Patent: Sep. 20, 1994

[54] PROCESS FOR DRYING $CH_2F_2$ REFRIGERANT UTILIZING ZEOLITE

[75] Inventors: Maryellen Lavin, Tarrytown, N.Y.; Alan P. Cohen, New Fairfield, Conn.; Nanette Greenlay, Port Chester, N.Y.; Thomas R. Cannan, Congers, N.Y.; Richard J. Hinchey, Thornwood, N.Y.

[73] Assignee: UOP, Des Plaines, Ill.

[21] Appl. No.: 171,959

[22] Filed: Dec. 23, 1993

[51] Int. Cl.$^5$ ............................................. F25B 47/00
[52] U.S. Cl. ............................................. 62/85; 210/689
[58] Field of Search ..................... 62/85, 475; 210/689

[56] References Cited

U.S. PATENT DOCUMENTS 4,637,881 1/1987 Sciuto .................................. 210/689
5,161,385 11/1992 Schumacher ........................ 62/475

*Primary Examiner*—John M. Sollecito
*Attorney, Agent, or Firm*—Thomas K. McBride; Richard G. Miller; Richard P. Silverman

[57] ABSTRACT

Difluoromethane (R32) is of current interest as a partial replacement for chlorodifluoromethane (R22) refrigerant heretofore widely used in vapor compression refrigeration systems. R32 has, however, proved to be more reactive than is desirable with the zeolite A adsorbent-desiccant compositions used in such systems to prevent corrosion and freeze-up problems. The sodium cation form of a zeolite having the crystal structure of zeolite B is found to be an effective adsorbent for that purpose and to be significantly less reactive with the R32.

5 Claims, 2 Drawing Sheets

PROCESS FOR DRYING CH₂F₂ REFRIGERANT UTILIZING ZEOLITE

FIELD OF THE INVENTION

The present invention relates in general to the removal of water from refrigerant mixtures containing difluoromethane (HFC-32) and more particularly to the treatment of such mixtures employed as circulating refrigerant streams of refrigeration systems to sequester water and decomposition products of the refrigerant as a means for avoiding freeze-ups and corrosion. The treatment comprises adsorption of these impurities on a zeolitic molecular sieve having the crystal structure of zeolite B.

BACKGROUND OF THE INVENTION

In view of the now well-established relationship between chlorofluorocarbons (CFC's) released into the atmosphere and the depletion of the earth's ozone layer, considerable attention is being directed to finding effective substitutes for these once widely used compounds. It appears that the worst offenders are the fully halogenated CFC's which contain chlorine. These compounds are relatively unreactive with other compounds in the lower atmosphere and thus are able to diffuse into the stratosphere intact and be decomposed by ultraviolet radiation to form, inter alia, chlorine compounds which readily react with ozone. On the premise that it is the chlorine constituent of the CFC's which ultimately reacts with and destroys the ozone molecules, and in the interest of approximating as closely as possible the physical properties of the CFC's already in use, the proposed substitutes have in general been HCFC's containing lesser proportions of chlorine or fluorocarbons containing no chlorine at all. For example, dichlorodifluoromethane, widely used under the trademark Freon 12 as a refrigerant in household refrigerators, in automotive units and in commercial freezers and display cases, has been replaced in many instances by 1,1,1,2-tetrafluoroethane (also known as R-134a) or by chlorodifluoromethane (also known as R22 or HCFC-22). Because R-134a is not miscible with many commonly used lubricants, mixtures of R-134a and R22 have been proposed for systems employing lubricants soluble in R22. See U.S. Pat. No. 5,198,139, Bierschenk et al, in this regard. In the recent past, over 90% of the chlorodifluoromethane and about a third of the dichlorodifluoromethane manufactured was utilized in air-conditioning and refrigeration.

With increasing recognition of the seriousness of atmospheric ozone depletion, stricter limitations on the future use of any chlorine-containing refrigerant continue to be imposed. One of the most suitable replacements for R22 in stationary refrigeration systems is a non-flammable mixture of the HFC compound difluoromethane, also known as R32, with other halocarbons or halohydrocarbons such as R134a and R125 ($C_2HF_5$). One such mixture has been proposed which consists of 60% R32 and 40% R125. Another proposed mixture consists of 30% R32, 10% R125 and 60% R134a. A significant problem in making this substitution arises from the fact that R32 is more reactive than R22 with the zeolite A commonly employed as an adsorbent-desiccant in the circulating refrigerant stream to protect against freeze-ups and corrosion of the refrigeration unit.

SUMMARY OF THE INVENTION

It has now been discovered that the sodium cation form of an activated zeolitic molecular sieve which has the crystal structure of zeolite B and a framework Si/Al₂ molar ratio of at least 2.5, and preferably at least 5.0, possesses the requisite selectivity and adsorption capacity for effectively removing water from R32 refrigerant and exhibits a relatively low reactivity with the HFC under the conditions encountered in use in a refrigerant recycle stream such as employed in a stationary refrigeration unit. Of the various cation forms of zeolite B, the sodium form is found to have the most favorable combination of properties necessary for effective R32 drying. These properties include pore openings small enough to significantly limit, though not totally prevent, the passage of R32 molecules, a relatively large capacity for water vapor adsorption and the ability to withstand the thermal and hydrothermal stresses of being incorporated into engineered agglomerate forms. It also has the distinct commercial advantage of being the cation form of the as-synthesized zeolite B.

Accordingly, in a vapor compression refrigeration process wherein a refrigerant fluid comprising difluoromethane is cycled within a closed system and is alternately vaporized and condensed in the known manner to produce cooling, the present invention provides an improvement which comprises incorporating within the closed system containing said difluoromethane and in contact therewith as a desiccant the sodium cation form of an activated zeolitic molecular sieve having the crystal structure of zeolite B, said zeolite B having a framework Si/Al₂ molar ratio of at least 2.5, and preferably having at least 75 percent of its $AlO_2^-$ framework tetrahedral units associated with sodium cations. More preferably, substantially the entire cation population are sodium cations.

DETAILED DESCRIPTION OF THE INVENTION

Figure 1:
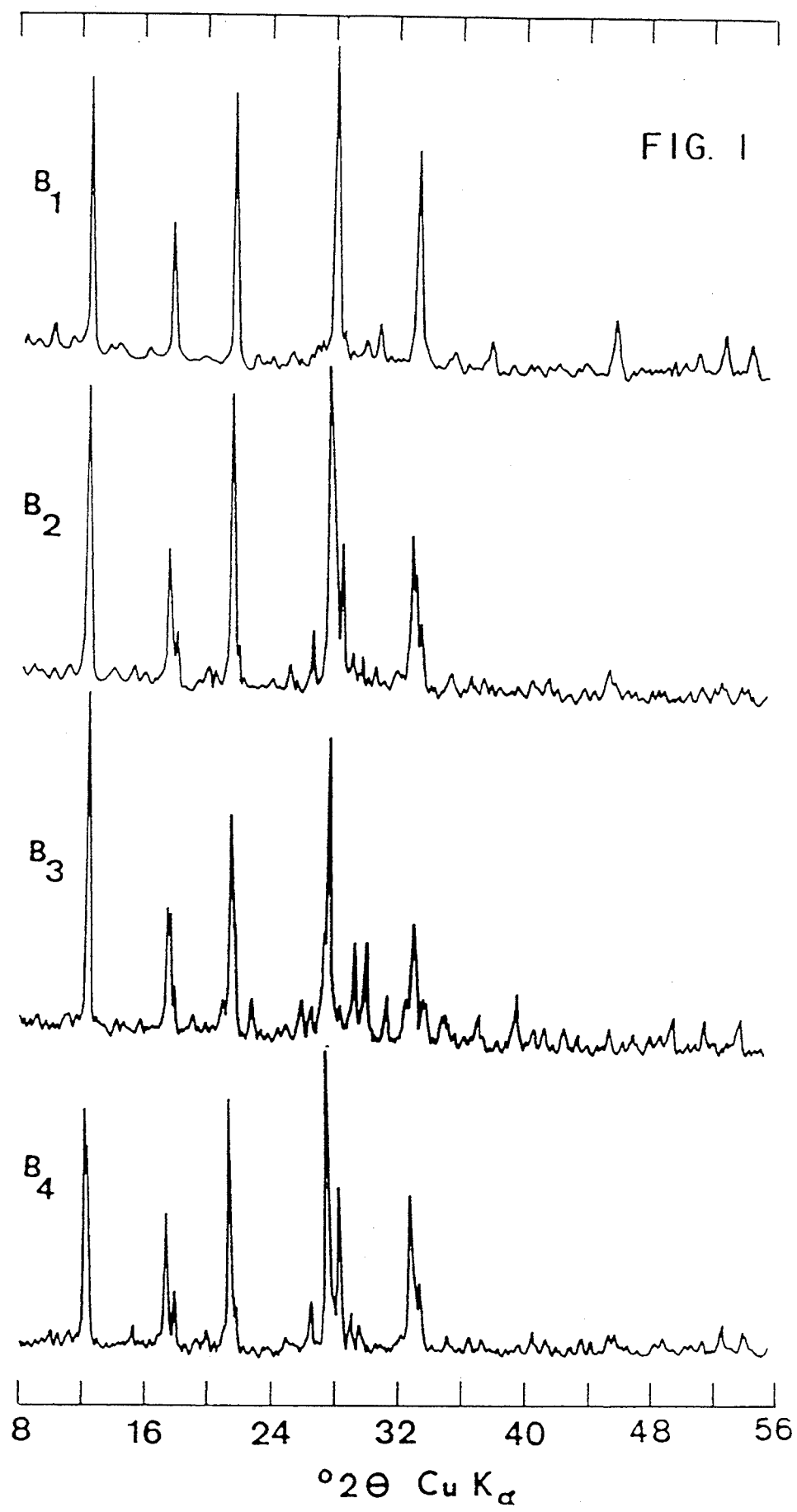
FIGS. 1 and 2 consists of the respective x-ray powder diffraction patterns of various crystalline forms of zeolite B.
Figure 2:
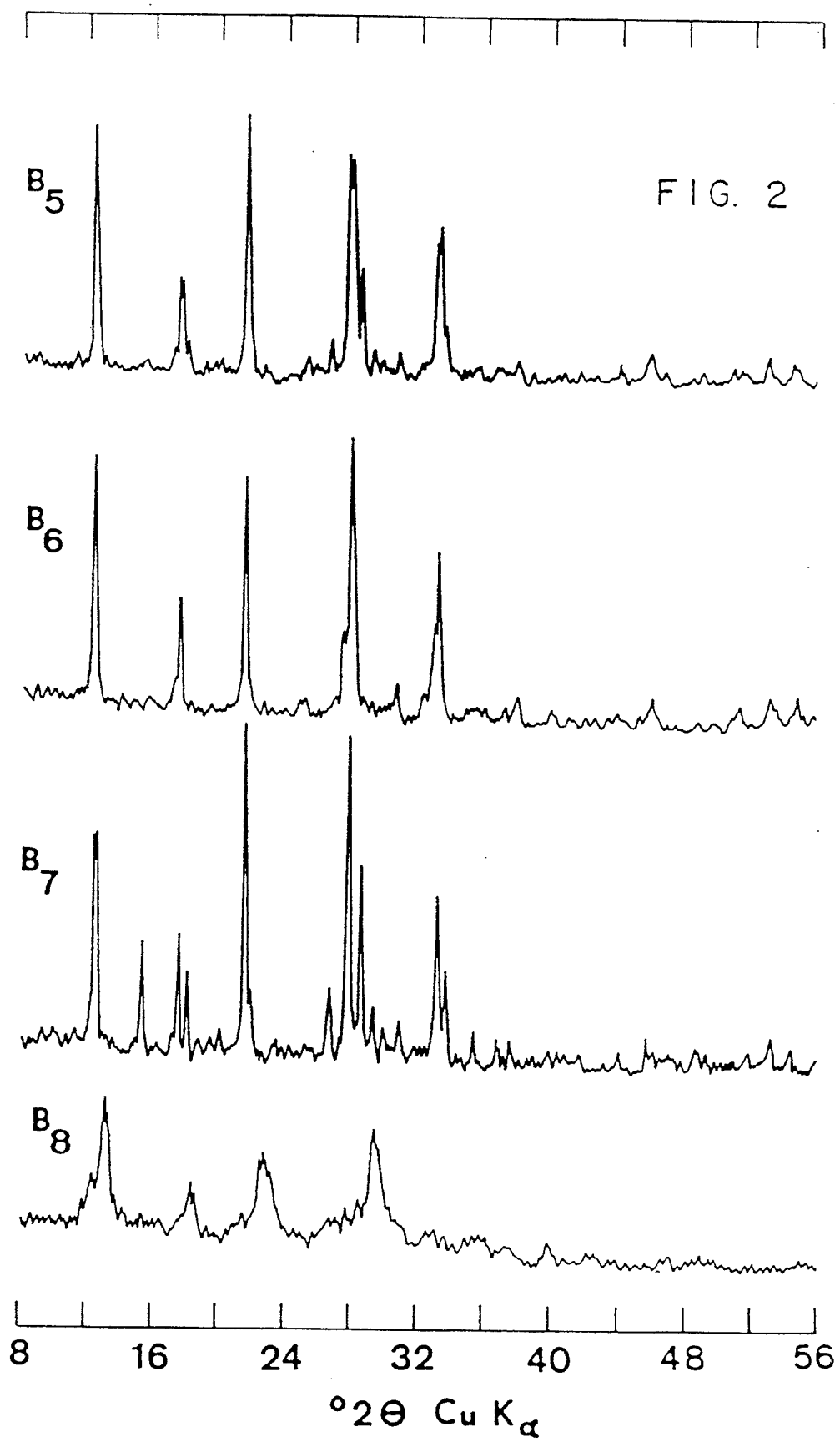

Ideally a purified and dried refrigerant fluid, after having been sealed in a refrigeration unit, would continue to circulate through the compressors, Joule-Thompson nozzles, cooling coils, etc., for the life of the unit without causing any corrosion or freeze-up problems. In practice, however, the system can rarely be so thoroughly sealed, or the components so thoroughly dried before sealing, to prevent water and other contaminants from entering the sealed system, and these materials must be removed or sequestered to avoid the development of the aforementioned problems. Conventionally the contaminants are rendered innocuous by adsorption on a suitable adsorbent inserted into the sealed system in contact with the circulating refrigerant stream. In the case of halocarbon refrigerants the contaminants of greatest concern, in addition to water, are attributable to the degradation products of the refrigerant molecules themselves. Halogen acids, notably HCl, can form and cause corrosion. In some instances, the adsorbent composition itself can be a reactant in the chemical reactions which result in the production of corrosive products. Zeolitic molecular sieves generally exhibit this property and, accordingly, it is necessary to select the particular zeolite adsorbent in view of the physical and chemical properties of the refrigerant involved to minimize harmful reactions. Since essentially all of the active sites of a zeolite are reachable only by molecules which can enter the internal cavities of the crystal structure through its uniform pore system, it is advantageous to employ a zeolite whose pore openings admit water and other small impurity molecules, but exclude molecules of the refrigerant. Thus, a commonly used adsorbent for refrigeration systems is a highly exchanged potassium cation form of zeolite A having pore diameters of about 3 Angstroms. The effective pore diameters can be further reduced, to a slight degree, by controlled steaming. A potassium cation exchanged (40%) form of zeolite A, i.e., zeolite 3A, has been found to be quite effective in drying R-134a and R22, for example.

R-32, however, is both smaller in molecular size and more polar than R22 by virtue of the substitution of a hydrogen atom for the chlorine atom in chlorodifluoromethane. It is also more reactive than R22 with constituents in the lower atmosphere and thus, advantageously, is less likely to escape unreacted into the stratosphere. It is, by the same token, more reactive with zeolites, including zeolite 3A, having pores large enough for R32 to enter. The greater polarity of R32 also means that the partial blocking of zeolite pores by cation exchange techniques is less effective in excluding the R32 from the inner cavities of the zeolite crystal structure.

The sodium cation form of a zeolite having the crystal structure of zeolite B, and having a framework $Si/Al_2$ molar ratio of at least 2.5, is found to be highly effective as a desiccant-adsorbent when employed in R32 refrigerant streams. This zeolite composition has the advantage of having a very small effective pore diameter and, particularly in those forms having a higher $Si/Al_2$ molar ratio, a lower overall framework charge compared with zeolite A. These properties tend to limit access to the pore system of the R32 refrigerant and lessen the reaction with the R32 molecules to produce reaction products corrosive toward the refrigeration system and destructive of the adsorbent itself. The adsorption capacity of the zeolite for water is, on the other hand, entirely adequate for its intended use. For example a NaB composition having a $Si/Al_2$ molar ratio of 5.0 is able to adsorb 19.5 weight percent water vapor at 25° C. and 4.6 torr water pressure after activation at 400° C. A similarly activated zeolite B is found to adsorb nil difluoromethane at 500 torr pressure and 25° C. The adsorption capacity for water for other cationic forms is in general the same as for NaB, but many of the various cation forms of zeolite B cannot be activated fully or at temperatures above about 200° C. without suffering a loss of crystallinity. For example, the $Zn^{++}$-, $Mg^{++}$- and $Li^{30}$-exchanged forms of NaB, even at relatively low levels of ion-exchange, become x-ray amorphous when activation is attempted even at a temperature as low as 250° C. By the term activation is meant the removal of at least a major proportion of the water of hydration present in the crystal void space as a consequence of synthesis. Further, the pore diameters of other alkali metal cation forms of zeolite B are large enough to freely admit R32 into the inner cavities of the zeolite structure, thus permitting an unacceptable degree of reaction between the zeolite and the R32.

The zeolite adsorbent generally referred to as zeolite B is in fact a series of microporous crystalline aluminosilicates whose crystal structures have the same chemical bonds but have differences in bond angles due to displacive transformations, i.e., changes through rotation of structural sub-units. The crystal framework is remarkably flexible, and the displacive transformations produce marked changes in the lattice constants. At least eight members of the series have been identified and denominated as $B_1$ through $B_8$. The composition denominated $B_1$ has a body-centered cubic structure and is the same as the composition denominated as Na—$P_1$ by Barrer et al [J. Chem. Soc., 1521–28 (1959)]. The $B_2$, $B_3$, and $B_6$ members have body-centered tetragonal structures with varying degrees of displacive transformation of the body-centered cubic structure of $B_1$. Members $B_4$ and $B_7$ resemble the tetragonal primitive structure characteristic of the phase denominated Na—$P_t$ by Taylor and Roy [Am. Mineral. 49, 656–682 (1964)]. Member $B_8$ was formed by drying $B_1$ in air at 120° C. This partially dehydrated form exhibits major x-ray diffraction lines which are displaced considerably from the lines of the Bpattern. Upon rehydration the $B_8$ member reverts to the $B_1$ structure. The x-ray powder diffraction patterns of these series members are shown in drawings.

The syntheses of zeolite B in the various forms referred to hereinabove are disclosed in detail in the Taylor and Roy literature article cited above and in U.S. Pat. No. 3,008,803, issued Nov. 14, 1961, to R. M. Milton, and also in the W. C. Beard literature article in "Advances in Chemistry, Series 101," American Chemical Society, Wash. D.C., pgs. 237–249 (1971). These publications are incorporated by reference herein.

In view of the foregoing, the zeolite adsorbent utilized in the process of the appended claims is an activated microporous aluminosilicate zeolite which has a $Si/Al_2$ molar ratio of at least 2.5 and in its fully hydrated state has an x-ray diffraction pattern the major d-spacings of which are

| d, Å | Relative Intensity |
| --- | --- |
| 7.10 ± 0.1 | S–VS |
| 4.97 ± 0.1 | M–S |
| 4.10 ± 0.1 | S–VS |
| 3.18 ± 0.1 | S–VS |

In terms of $I/I_r \times 100$, the relative intensities designated VS (very strong), S (strong) and M (medium) are within the ranges (80–100), (60–79) and (40–59), respectively.

For use as a desiccant-adsorbent in R32 refrigerant streams the zeolite B crystals are agglomerated into engineered forms to avoid entrainment in the stream and plugging of orifices and conduits and abrasive damage to the refrigeration system. While compaction to create self-bonding of the crystal particles is possible, it is advantageous to utilize binder materials to create agglomerates of high attrition resistance. It has been determined, in this regard, that the choice of binder material can be an important factor in inhibiting the reactivity of the R32 with the adsorbent agglomerates. For example, clays exhibiting significant degrees of basicity react with the R32 in essentially the same manner as the basic NaB zeolite. Ideally the clay binder should be neither basic nor acidic and require modest calcination temperatures to be set. Unfortunately no commercially available clay has been found to possess all of these properties. Without wanting to be bound by any particular theory, it is possible that R32 reacts with basic zeolitic aluminosilicates, such as zeolite NaB, according to the following equations:

$$CH_2F_2 + Na(-Si-O-Al-) \rightarrow (CHF_2)^- + H(-Si-OAl-) \quad 1.$$

Dealumination 2.

$$(CHF_2)^- + CH_2F_2 \rightarrow F_2HC-CFH_2 + F^- \quad 3.$$

$$Al^{+3} + 6F^- \rightarrow (AlF_6)^{-3} \quad 4.$$

$$Si^{+4} + 6F^- \rightarrow (SiF_6)^{-2} \quad 5.$$

Presumably similar reactions occur between $CH_2F_2$ and the various clay compositions commonly used as binder material. These reactions do not, however, occur with equal facility among the various clays. For example, in an experimental procedure wherein liquid $CH_2F_2$ was contacted with a sample of avery clay [ideal formula $Al_2(Si_2O_5)(OH)_4$] and a sample of attapulgite clay [ideal formula $Mg_5Si_8O_{20}(OH)_2 \cdot 8H_2O$] at 75° C. and the vapor pressure of R32 at that temperature (~53 atmospheres) for 7 days, post-treatment analysis of the avery clay indicated a 0.67 wt. % fluoride content versus a 1.23 wt. % fluoride content for the attapulgite. Sepiolite and halloysite appear to resemble attapulgite and avery clay, respectively, in their reactivity toward $CH_2F_2$. The firing temperatures necessary to achieve adequate bonding exceed 550° C. for halloysite and avery clays. These temperatures cause undue thermal and hydrothermal degradation of the NaB. The significantly lower firing temperature required for attapulgite makes it a preferred binding material for NaB agglomerates.

EXAMPLE 1.

In order to verify the suitability of zeolite B for use in the present process, a refrigerant/desiccant compatibility test was carried out in which a mixture of liquid R32 and a polyester lubricant were contacted with NaB in a stainless steel bomb. In carrying out the test, 15 grams of 1/16" activated pellets of NaB zeolite having a Si/Al2 ratio of 5.0 bonded with 20 weight percent attapulgite clay were first added to the bomb followed by the injection of 1 gram of the lubricant and lastly by a charge of 10 grams of the R32 refrigerant in the liquid phase. Air was evacuated from the bomb after adding lubricant but before charging with refrigerant. The temperature of the sealed bomb was raised to 75° C. and retained in that state for 7 days. Thereafter the NaB pellets were recovered and adsorbed R32 refrigerant was removed from the zeolite pores by first grinding the zeolite particles, permitting the ground solids to hydrate in open air for a period of about 11 days. The residual fluorine content, believed to be in the form of fluoroaluminate and fluorosilicate, is a measure of the degree to which the R32 reacted with the NaB adsorbent. It was found by chemical analysis that the fluorine content was about 1200 ppm (wt.). This value is quite favorable when compared with attapulgite-bonded beads of zeolite NaA (1.23 wt. % F.) and halloysite-bonded beads of zeolite KA (0.6 wt. % F.) when tested under essentially the same conditions.

EXAMPLE 2.

The ability of NaB to adsorb water present in low concentrations of R32 was determined under static conditions by contacting at 125° F. (51.7° C.) samples of NaB, preloaded with water, with liquid phase R32. In each instance the R32 water composition was maintained in contact with the zeolite for 20 hours at the test temperature. It was determined by analysis that the water loading on the zeolite following contact was 6.7 Wt. %, 10.4 wt. % and 16.3 wt. %. Analysis of water content of R32 was 3 ppm (wt), 166 pm (wt), and 308 ppm (wt), respectively.

What is claimed is:

1. In a refrigeration process wherein a refrigerant fluid comprising difluoromethane is cycled within a closed system and is alternately vaporized and condensed in a manner to produce cooling, the improvement which comprises incorporating within the closed system containing said difluoromethane and in contact therewith as a desiccant, an activated sodium cation form of a microporous zeolitic molecular sieve having the crystal structure of zeolite B, a framework $Si/Al_2$ molar ratio of at least 2.5, and in the fully hydrated state an x-ray diffraction pattern the major d-spacings of which are

| d, Å | Relative Intensity |
|---|---|
| 7.10 ± 0.1 | S-VS |
| 4.97 ± 0.1 | M-S |
| 4.10 ± 0.1 | S-VS |
| 3.18 ± 0.1 | S-VS. |

2. Process according to claim 1 wherein the $Si/Al_2$ molar ratio of the zeolitic molecular sieve is at least 5.0.

3. Process according to claim 1 wherein at least 75 percent of the zeolitic cations are sodium.

4. Process according to claim 2 wherein substantially all of the metal cations of the zeolite are sodium.

5. Process according to claim 2 wherein the zeolitic molecular sieve is bonded agglomerate in which the bonding agent is attapulgite clay.

* * * * *